(12) United States Patent
Quint (10) Patent No.: US 12,089,954 B2
(45) Date of Patent: Sep. 17, 2024

(54) MULTIFUNCTIONAL USE OF AN ELECTRODE STRUCTURE OF A BALLOON CATHETER SYSTEM

(71) Applicant: BIOTRONIK AG, Bülach (CH)

(72) Inventor: Bodo Quint, Dettighofen (DE)

(73) Assignee: BIOTRONIK AG, Buelach (CH)

(*) Notice: Subject to any disclaimer, the term of this patent is extended or adjusted under 35 U.S.C. 154(b) by 727 days.

(21) Appl. No.: 17/289,866

(22) PCT Filed: Nov. 18, 2019

(86) PCT No.: PCT/EP2019/081636
§ 371 (c)(1),
(2) Date: Apr. 29, 2021

(87) PCT Pub. No.: WO2020/104368
PCT Pub. Date: May 28, 2020

(65) Prior Publication Data
US 2021/0401375 A1    Dec. 30, 2021

(30) Foreign Application Priority Data
Nov. 22, 2018   (DE) ............... 10 2018 129 435.2

(51) Int. Cl.
*A61B 5/00*      (2006.01)
*A61B 5/0538*    (2021.01)
(Continued)

(52) U.S. Cl.
CPC .......... *A61B 5/6853* (2013.01); *A61B 5/0538* (2013.01); *A61B 5/068* (2013.01);
(Continued)

(58) Field of Classification Search
CPC ..... A61B 5/6853; A61B 5/0538; A61B 5/068; A61B 5/25; A61B 5/6886;
(Continued)

(56) References Cited

U.S. PATENT DOCUMENTS 9,545,510 B2    1/2017  Kokones et al.
2010/0010612 A1  1/2010  Gelbart et al.
(Continued)

OTHER PUBLICATIONS

International Search Report and Written Opinion from the corresponding International Patent Application No. PCT/EP2019/081636, dated Feb. 11, 2020.

*Primary Examiner* — David J. McCrosky
(74) *Attorney, Agent, or Firm* — Greer, Burns & Crain, Ltd.; Steven P. Fallon (57) ABSTRACT

A balloon catheter system has a balloon extending in an axial direction and surrounding a balloon interior. The balloon has an outer side facing away from the balloon interior. A catheter is connected to the balloon and extending in the axial direction, the catheter having a lumen in fluid communication with the balloon interior. First and second annular electrodes are disposed on the outer side, each extending in a circumferential direction of the balloon and being located opposite one another in the axial direction. The electrodes are configured to measure one of more of strain of the balloon in the circumferential direction, strain of the balloon in the radial direction, an impedance of tissue of a patient resting against the electrodes, and a redox potential of tissue of the patient contacting at least one of the electrodes.

17 Claims, 4 Drawing Sheets

(51) Int. Cl.
  *A61B 5/06*    (2006.01)
  *A61B 5/25*    (2021.01)
  *A61F 2/958*   (2013.01)
  *A61M 25/10*   (2013.01)

(52) U.S. Cl.
  CPC .............. *A61B 5/25* (2021.01); *A61B 5/6886* (2013.01); *A61F 2/958* (2013.01); *A61M 25/10184* (2013.11); *A61B 2562/0209* (2013.01); *A61F 2250/001* (2013.01); *A61M 2205/3303* (2013.01); *A61M 2205/3317* (2013.01); *A61M 2205/332* (2013.01); *A61M 2205/3327* (2013.01); *A61M 2205/3344* (2013.01); *A61M 2230/65* (2013.01)

(58) Field of Classification Search
  CPC ........... A61B 2562/0209; A61B 5/1473; A61F 2/958; A61F 2250/001; A61M 25/10184; A61M 2205/3303; A61M 2205/3317; A61M 2205/332; A61M 2205/3327; A61M 2205/3344; A61M 2230/65
  See application file for complete search history.

(56) References Cited

U.S. PATENT DOCUMENTS

| | | |
|---|---|---|
| 2013/0123694 A1 | 5/2013 | Subramaniyan et al. |
| 2015/0005762 A1 | 1/2015 | Belk et al. |
| 2016/0051325 A1 | 2/2016 | Hooven |
| 2018/0036072 A1 | 2/2018 | Mathur et al. |

MULTIFUNCTIONAL USE OF AN ELECTRODE STRUCTURE OF A BALLOON CATHETER SYSTEM

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2019/081636, which was filed Nov. 18, 2019, which application claimed priority from German Application Serial Number 10 2018 129 435, which was filed Nov. 22, 2018.

FIELD OF THE INVENTION

The present invention relates to balloon catheter systems, in particular for implanting a stent.

BACKGROUND

Balloon catheter systems typically include a balloon formed from a balloon envelope that extends in an axial direction, surrounds a balloon interior of the balloon and has an outer side facing away from the balloon interior. Such balloon catheter systems furthermore include a catheter that is connected to the balloon and extends in the axial direction and that has a lumen through which the balloon interior can be filled with a fluid medium for expanding the balloon. A stent is crimped onto the outer side of the balloon (that is, the stent, which is compressed in the radial direction, sits on the outer side) and can be expanded in a vessel of a patient (in the radial direction) by expansion of the balloon at an implantation site, and thereby be anchored in the vessel at the implantation site.

Often, it is desirable to equip such balloon catheter systems with an additional sensor system to improve control over the stent during the expansion of the stent or during the release of the stent.

For example, the impedance behavior of vascular tissue is examined in Sungbo Cho: "Electrical Impedance Spectroscopy for Characterization of Vessel Wall" VDM Publishing (2009) ISBN 978-3-639-20741-5.

U.S. Pat. No. 9,545,510 describes a lead having directional electrodes for stimulating tissue.

US 2016/0051325 describes a device for remodeling tissue lumen by electrodes.

US 2018/0036072 describes a method for expanding a balloon in the renal artery, wherein bipolar electrode pairs are electrically coupled with a wall of the renal artery so as to therapeutically alter at least one nerve in the vicinity of the rental artery.

SUMMARY OF THE INVENTION

A preferred balloon catheter system has a balloon extending in an axial direction and surrounding a balloon interior. The balloon has an outer side facing away from the balloon interior. A catheter is connected to the balloon and extending in the axial direction, the catheter having a lumen in fluid communication with the balloon interior. First and second annular electrodes are disposed on the outer side, each extending in a circumferential direction of the balloon and being located opposite one another in the axial direction. The electrodes are configured to measure one of more of strain of the balloon in the circumferential direction, strain of the balloon in the radial direction, an impedance of tissue of a patient resting against the electrodes, and a redox potential of tissue of the patient contacting at least one of the electrodes.

BRIEF DESCRIPTION OF THE DRAWINGS

Features, advantages and embodiments of the present invention shall be described hereafter based on the figures. In the drawings.

DETAILED DESCRIPTION OF THE PREFERRED EMBODIMENTS

Within the meaning of the present invention, the term 'tissue' encompasses both vascular tissue of the patient and blood of the patient.

Within the scope of the present invention, the term 'annular' denotes that the corresponding electrode can have an open annular design or a closed annular design. In the case of an open annular electrode, the electrode has an interruption or a gap. In particular, in a balloon that is expanded (in the radial direction), the open annular electrode then extends in a circular arc shape in the circumferential direction of the balloon, wherein a corresponding central angle of the arc of the circle or of the particular electrode is at least 300°, in particular at least 310°, in particular at least 320°, in particular at least 330°, in particular at least 340°, and in particular at least 350°.

Heretofore, the viscoelastic behavior of a balloon of a balloon catheter system is not specified, explained or displayed to a physician during the implantation of a stent. In practice, however, this potentially results in inadequate precision with respect to the control of the diameter of the balloon when used in the patient. Depending on the catheter design, viscoelastic properties of the balloon component are heavily dependent on the viscoelastic properties of the balloon material that is used, but also physical conditions during manufacturing and component loading that has already occurred. From a technical point of view, elastomer modified balloon materials in general have improved fixation properties to stent components as well as a more intensified viscoelastic behavior.

For measuring the strain and/or the impedance and/or the redox potential, the balloon is, in particular, in a state in which the balloon has been inserted into a vessel of a patient, wherein the balloon is, in particular, located at the planned implantation site or in the surrounding to area of this implantation site.

The measurement of said impedance using the two electrodes advantageously allows, for example, the detection of full vascular contact of the stent with the surrounding vessel wall during the expansion of the balloon in the radial direction, and, for example, the option of is characterizing the contacting tissue, and in particular of the vascular tissue (for example, atherosclerotic state). The balloon or stent can thus be expanded more precisely.

The ascertainment of a redox potential advantageously allows, for example, the respiration of the patient to be tracked by detecting the modulation of the oxygen saturation of the patient's blood when this contacts the corresponding (second) electrode. So as to determine the redox potential, a differential measurement can be carried out, for example (using another identical electrode), or an electrochemical reference electrode is used, for example.

Moreover, detecting the strain of the balloon in the radial direction allows the state of the balloon to be controlled more precisely during expansion under pressure, for example, by using a first section of the first electrode as a strain gauge. In connection with the impedance measurement, this results in a synergy effect. For example, the full vessel contact of the balloon/stent can be ascertained in combination with the impedance measurement. In particular, the stent can be anchored in the vessel with defined dilation as a result of the strain detection. In this regard, what is known as "recoil" of the stent and the adaptation to the vessel geometry can be optimized.

The invention advantageously allows the actual dimension of the balloon to be tracked by sensors. This makes it possible, for example, to select thermal processes for producing the balloon, and also the choice of material of the balloon, in such a way that an expanded working range of the balloon catheter system is created. For example, a thermally heavily conditioned balloon or a strongly viscoelastic balloon material has very high compliance of the diameter during the first inflation. This can be utilized to adapt the balloon to vessel dimensions in an expanded range. Thereafter, however, the same balloon can also be precisely post-dilated since the aforementioned measurements (impedance and/or strain) provide a feedback signal with respect to the diameter of the balloon in the radial direction.

According to one embodiment of the balloon catheter system according to the invention, it is provided that the two electrodes are each formed by or as a coating of the outer side of the balloon with a precious metal, in particular gold. The precious metal or gold can have been applied to the outer side of the balloon by way of a known sputtering process, for example. Very thin precious metal or gold layers, applied by way of a sputtering process, advantageously exhibit suitable adhesion and moreover also show reversible extensibility.

In an alternative embodiment of the invention, one or both electrodes are formed by conductive ink. In this embodiment of the invention, the electrodes are advantageously printed onto the balloon using conductive ink. This embodiment can also be combined with the embodiment described above. Thin precious metal or gold layers can be vapor deposited onto the conductive ink in the process. The combination of the two embodiments is, in particular, suitable for the currentless determination of the redox potential.

According to one embodiment of the balloon catheter system according to the invention, it is furthermore provided that a stent is crimped onto the outer side of the balloon envelope, wherein the stent is expandable at an implantation site in a vessel of a patient by expansion of the balloon. The expansion of the balloon can be carried out by introducing the fluid medium into the balloon interior. In other words, the stent, when compressed, is disposed on the outer side of the balloon and, in particular, surrounds the balloon. As a result of the expansion of the balloon in the radial direction, the stent is accordingly radially expanded and released or anchored to the vessel wall.

According to one embodiment of the invention, it is furthermore provided that the two electrodes are spaced apart from the stent in the axial direction when the stent is disposed on the outer side of the balloon or crimped onto the outer side.

According to one embodiment of the invention, it is furthermore provided that the first electrode includes a first section extending in the circumferential direction, and a second section, which extends in the circumferential direction, runs along the first section and is located opposite the first section in the axial direction and spaced apart therefrom in the axial direction.

According to one embodiment, it is furthermore provided in this regard that the first section of the electrode has a (free) first end section and a second end section.

According to one embodiment of the balloon catheter system according to the invention, it is furthermore provided that the second section has a free first end section and a second end section, wherein the two second end sections of the first and second sections of the first electrode are (preferably integrally) joined to one another by a joining section that extends in the axial direction. In other words, the first electrode thus has a U-shaped progression.

According to one embodiment, it is furthermore provided that the second section of the electrode is disposed in the axial direction between the first section of the electrode and an annular region of the second electrode.

According to one embodiment of the balloon catheter system according to the invention, it is furthermore provided that the first section of the first electrode is covered by electrical insulation so as to, in particular, electrically insulate the first section of the electrode with respect to body tissue of the patient, and the like.

According to one embodiment of the balloon catheter system according to the invention, it is furthermore provided that the first section forms a strain gauge for measuring strain of the balloon envelope in the circumferential direction and/or in the radial direction.

As a result of the balloon being extended in the circumferential direction or in the radial direction, the geometry of the first section, and thus the electrical resistance thereof, changes. The balloon catheter system can include a measuring device, which ascertains this electrical resistance and, in particular, variables derived therefrom, such as the instantaneous diameter of the balloon (for example, during expansion of the balloon).

If, moreover, a central point on this "measuring bridge" is designed to have a large surface area or low resistance and no insulation with respect to the surrounding area of the balloon (for example, second section of the electrode), two electrical supply lines to this sensor surface are already present for an electrical sensor system for strain detection. This is the optimal configuration for an impedance measuring electrode, since one line can be used as a resistive supply line of the working current, and the second contacting as a non current-carrying contact for detecting the present voltage. In particular, gold serving as an inert surface without any noteworthy oxide layer, however, also represents a traditional electrode is form for detecting redox potentials. The two electrodes can thus be used to detect changes in strain, the redox potential of the blood/of the tissue, and to detect impedance.

According to one embodiment of the balloon catheter system according to the invention, it is furthermore provided that the electrical resistance of the first section is in the range of 100 ohm to 10000 ohm.

According to one embodiment of the catheter system according to the invention, it is furthermore provided that the first end section of the first section of the first electrode and the first end section of the second section of the first electrode are located opposite one another in the axial direction.

According to one embodiment of the catheter system according to the invention, it is furthermore provided that the first end section of the first section or of the strain gauge of the first electrode and the first end section of the second section of the first electrode are located opposite the joining section in the circumferential direction, so that a gap is present between the two first end sections and the joining section.

According to one embodiment of the balloon catheter system according to the invention, it is furthermore provided that the second electrode includes a protrusion, which projects from an annular region of the second electrode in the axial direction and, in the process, extends in the axial direction into the gap so that the protrusion of the second electrode is disposed in the circumferential direction between the joining section and the two first end sections of the first electrode.

According to one embodiment of the balloon catheter system according to the invention, it is furthermore provided that the first electrode has an open annular design and/or that the second electrode (in particular, said annular region) has a closed annular design, that is, extends around the outer side of the balloon in the circumferential direction in a self-contained manner.

According to one embodiment of the balloon catheter system according to the invention, it is furthermore provided that the second end section of the first section of the first electrode (or, alternatively, the joining section) forms a first contact region of the first electrode, which is, in particular, connected to a first conductor in an electrically conducting manner.

According to one embodiment of the catheter system according to the invention, it is furthermore provided that the protrusion forms a contact region of the second electrode, which is, in particular, connected to a second conductor in an electrically conducting manner.

According to one embodiment of the catheter system according to the invention, it is furthermore provided that the first end section of the first section of the first electrode forms a second contact region of the first electrode, which is, in particular, connected to a third conductor in an electrically conducting manner.

According to one embodiment of the catheter system according to the invention, it is furthermore provided that the balloon catheter system is designed to measure a voltage on the second contact region and to use this to measure the impedance of body tissue resting against the two electrodes.

For measuring the impedance, the balloon catheter system can include a measuring device that is connected to the three conductors and provides a current flowing across the first and second conductors for measuring the impedance, the current flowing between the two electrodes or across the body tissue to be measured contacting the two electrodes (for example, during expansion of the balloon or stent), wherein said voltage is measured on the second contact region, which is contacted by way of the third conductor.

According to one embodiment of the balloon catheter system according to the invention, it is furthermore provided that the balloon catheter system is designed to measure a voltage on the contact region of the second electrode for measuring a redox potential of tissue (in particular blood) contacting the second electrode. In this embodiment of the invention, the balloon catheter system is preferably configured so that a voltage-free determination of the redox potential by cyclic voltammetry is possible.

The contact region of the second electrode can be connected by way of the second conductor to said measuring device (or another or separate measuring device) for measuring the voltage or the redox potential. For the measurement of said redox potential, the balloon catheter system is preferably designed to use the first electrode as a shield electrode for shielding the second electrode.

Another aspect of the present invention relates to a method using a balloon catheter system according to the invention, wherein strain of the balloon in the circumferential direction of the balloon and/or in the radial direction of the balloon is measured by the first electrode (in particular, by the first section of the first electrode), and/or wherein an impedance of tissue of a patient (in particular, vascular tissue and/or blood of the patient) contacting the two electrodes is measured by the two electrodes, and/or wherein a redox potential of tissue of the patient (in particular, vascular tissue and/or blood of the patient) contacting the second electrode is measured by the second electrode.

In terms of the method, it is, in particular, advantageous to determine the impedance by the two electrodes, and particularly preferably in combination with the strain measurement by way of the first electrode, and to thereby determine the positioning of an implant (such as a stent) in the vessel. This embodiment can be used to ensure the correct implantation of the stent in the vessel, and in particular, it can thus be ensured that the stent was expanded sufficiently to be securely anchored in the vessel.

Figure 1:
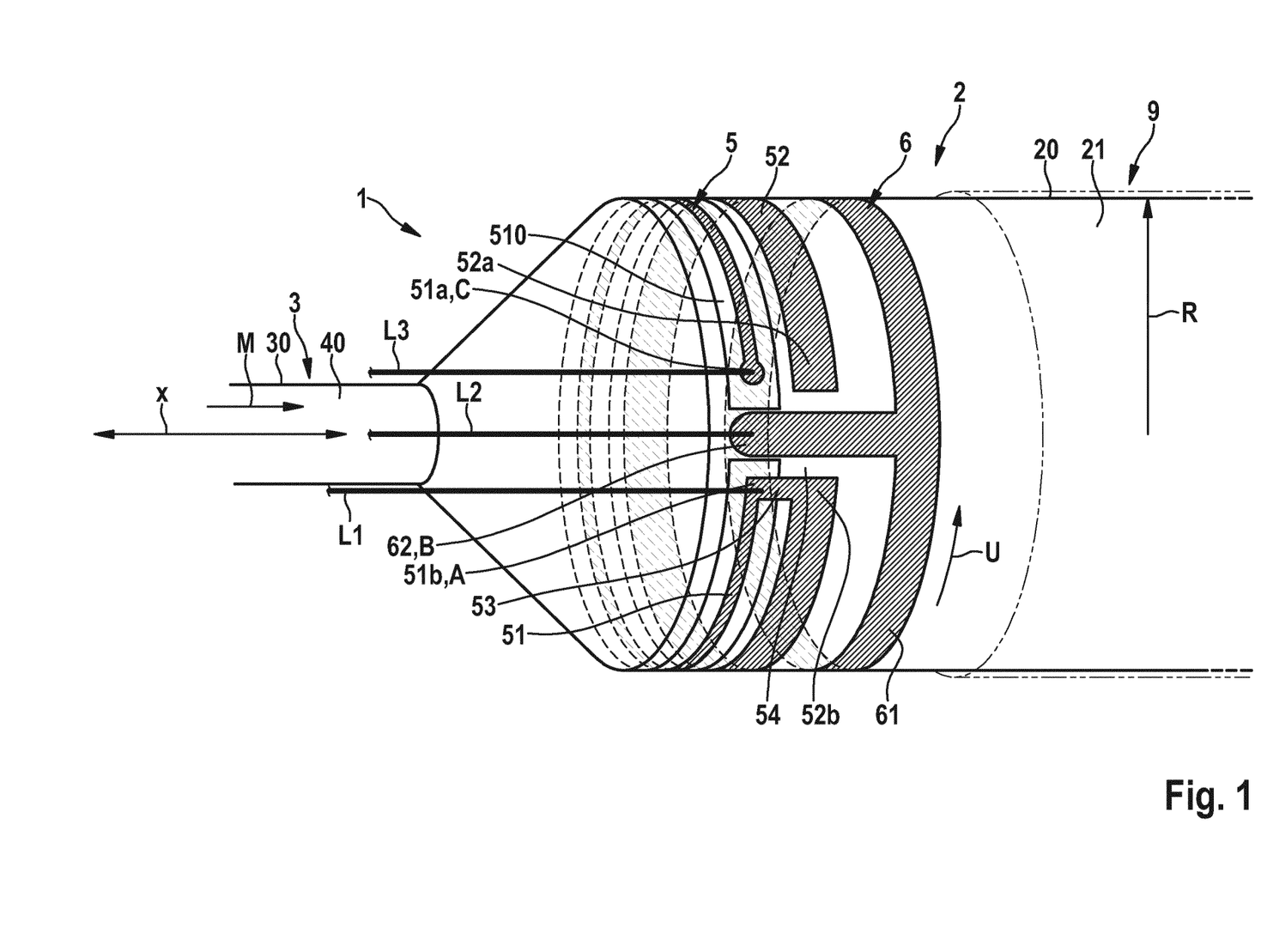
FIG. 1 shows a schematic sectional illustration of an embodiment of a balloon catheter system according to the invention, including a first and a second electrode, which are, in particular, configured for detecting the strain of the balloon and to measure the impedance and to measure the redox potential of tissue of the patient.
Figure 2:
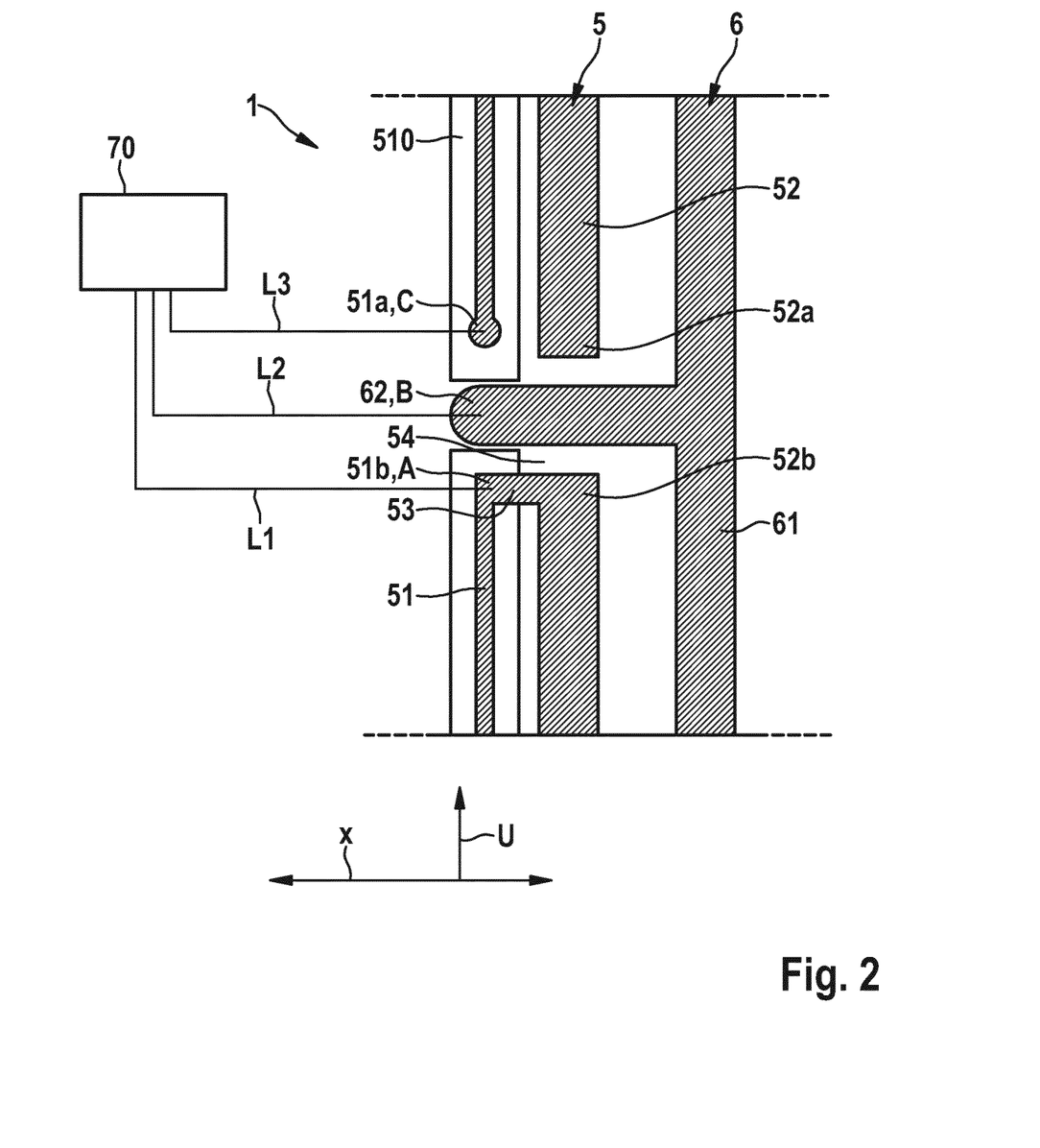
FIG. 2 shows a two-dimensional representation of the electrodes according to FIG. 1.

In connection with FIG. 2, FIG. 1 shows an embodiment of a balloon catheter system 1 according to the invention, including a balloon 2 that extends along a longitudinal axis x or in a corresponding axial direction x, surrounds a balloon interior 21 of the balloon 2 and has an outer side 20 facing away from the balloon interior 21. Furthermore, a flexible catheter 3 extending in the axial direction x is connected to the balloon 2, the catheter having a lumen 40 by way of which the balloon interior 21 can be filled with a fluid medium M for expanding the balloon 2 in a radial direction R of the balloon 2. The catheter 3 can include an outer shaft 30, which can be guided in a guide shaft 31. The lumen 40 is surrounded by the outer shaft 30. Moreover, the outer shaft 30 can surround a separate lumen for a guide wire 41 (see FIG. 5, for example). In particular, a stent 9, which by the catheter 3 or the balloon 2 can be is advanced to an implantation site in a vessel of the patient, is crimped onto the balloon 2, wherein the stent 9 can be expanded or dilated in the radial direction R by expanding the balloon 2 in the radial direction R (by introducing the medium M into the balloon interior 21).

According to the invention, it is now provided, as is apparent based on FIGS. 1 and 2, that the balloon 2 includes a preferably open annular first electrode 5 and a preferably closed annular second electrode 6, wherein the two electrodes 5, 6 are disposed on the outer side 20 of the balloon 2, each extend in a circumferential direction U of the balloon 2 and are located opposite one another in the axial direction x, and wherein the first electrode 5 is configured to measure strain of the balloon 2 in the circumferential direction U or in the radial direction R of the balloon 20, and/or wherein the two electrodes 5, 6 are configured to measure an impedance of tissue of a patient resting against the electrodes 5, 6, and/or wherein the two electrodes 5, 6 are configured to measure a redox potential of tissue of the patient contacting the second electrode 6.

According to FIG. 1 or 2, it is preferably provided that the first electrode 5 includes a first section 51 extending in the circumferential U and a second section 52, which extends along the circumferential direction U of the balloon 2, runs along the first section 51 of the first electrode 5 and is located opposite the first section in the axial direction x. The first section 51 of the first electrode 5 preferably has a first end section 51a and a second end section 51b. Likewise, the second section 52 of the first electrode 5 has a first end section 52a and a second end section 52b, wherein the two second end sections 51b, 52b of the first electrode 5 are integrally joined to one another by way of a joining section 53 of the first electrode 5 which extends in the axial direction x.

So as to configure a strain gauge 51, the first section 51 of the first electrode 5 is now covered by electrical insulation 510. In contrast, the second section 52 is exposed and can contact surrounding tissue or blood of the patient (for example, during the implantation).

Moreover it is, in particular, provided that the first end section 51a of the first section 51 of the first electrode 5 and the first end section 52a of the exposed second section 52 of the first electrode 5 are located opposite one another in the axial direction x, wherein furthermore the two first end sections 51a, 52a are located opposite the joining section 53 in the circumferential direction U, so that a gap 54 is present between the two first end sections 51a, 52a and the joining section 53. A protrusion 62 of the second electrode 6, which projects from an annular region 61 of the second electrode 6 in the axial direction x, projects into this gap 54 in the axial direction x. The protrusion 62 of the second electrode 6 is thus disposed in the circumferential direction U between the joining section 53 of the first electrode 5 and the two first end sections 51a, 52a of the first electrode 5.

For carrying out the measurements described herein, the electrode arrangement 5, 6 includes corresponding contact regions A, B, C.

In detail, it is preferably provided in this regard that the second end section 51b of the first section 51 (strain gauge) of the first electrode 5 forms a first contact region A of the first electrode 5, which is electrically contacted by a first conductor L1. Moreover, the protrusion 62 forms a contact region B of the second electrode 6, which is, in particular, electrically contacted by a second conductor L2. Furthermore, the first end section 51a of the first section 51 of the first electrode 5 forms a second contact region C of the first electrode 5, which is electrically contacted by a third conductor L3.

Figure 3:
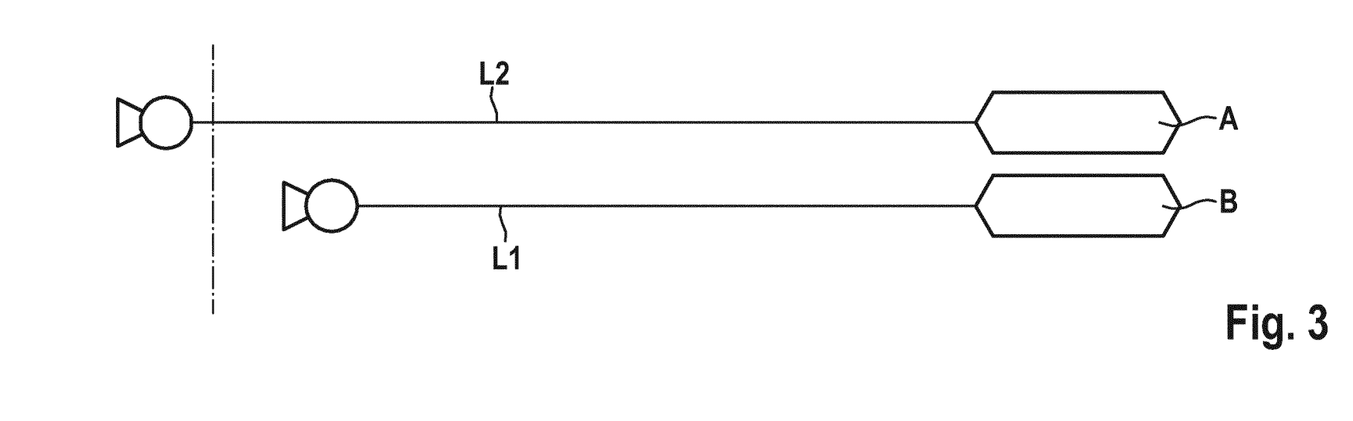
FIG. 3 shows a schematic representation of an impedance measurement by the two electrodes.
Figure 4:
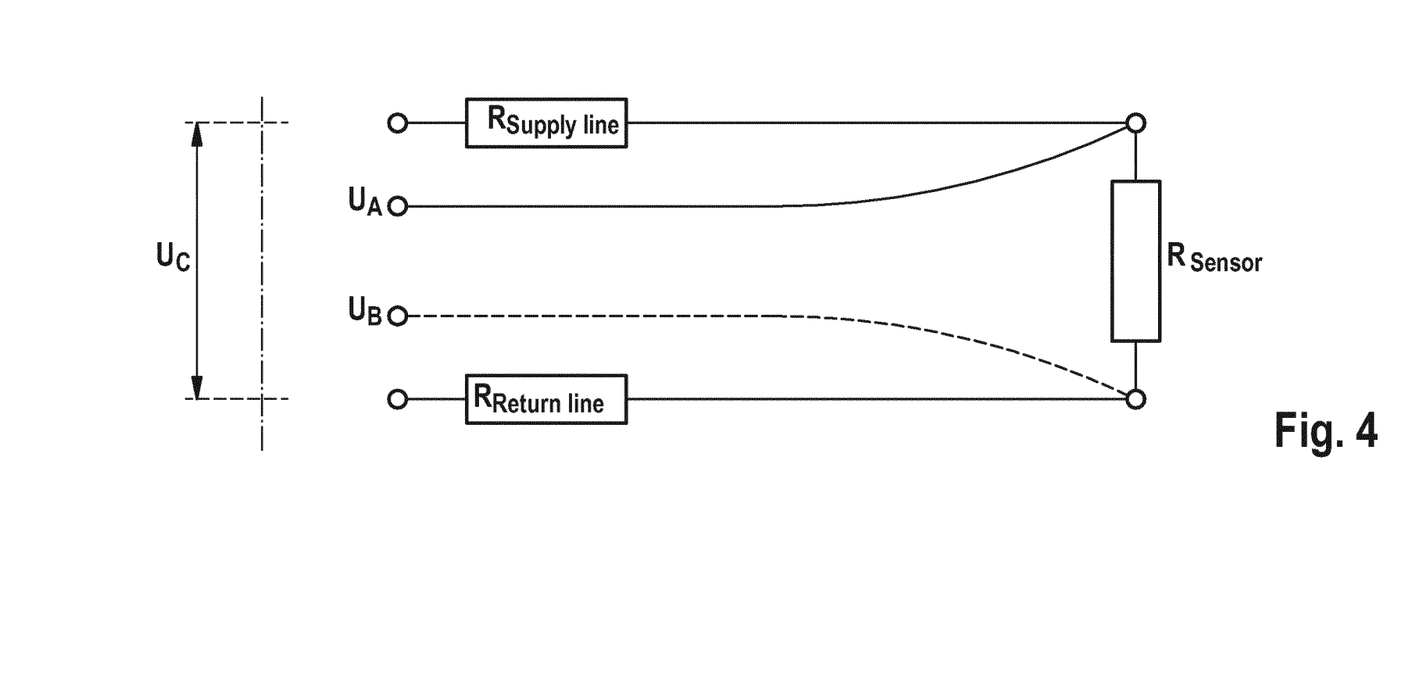
FIG. 4 shows an equivalent circuit of the impedance measurement corresponding to FIG. 3.

According to one embodiment, it is provided that the points or contact regions A and B are contacted with identical electrical impedance. If the two electrodes 5, 6 are now contacted by way of the contact regions A and B for an impedance measurement with the current flow of an impedance measurement, an impedance (also, contacting impedance) can be detected by measuring the voltage Uc across the contact region or point C, which can be utilized for more precisely ascertaining the tissue impedance (blood—tissue contact—atherosclerotic tissue contact). The comparatively close arrangement of the two electrodes 5, 6 in the axial direction x forces the current flow I across tissue regions close to the balloon, and in particular vascular tissue. The two electrodes 5, 6 preferably have a distance that is less than the thickness of the vessel wall of the vessel to be analyzed. In this embodiment, the electrodes 5, 6 have a distance of up to 0.1 mm. A schematic measuring arrangement, using the contact regions A, B or C, is shown in FIG. 3, wherein FIG. 4 shows a corresponding equivalent circuit. Said impedance (contacting impedance) $R_{Sensor}$ results, on the condition that $R_{Supply\ line}=R_{Return\ line}$ (see above), in the case of currentless measurement of $U_A$ as $R_{Sensor}=(U_A-U_B)/I=(U_C-2*(U_C-U_A))/I$.

So as to determine said impedance $R_{Sensor}$, an additional voltage signal $U_A$ is detected accordingly (apart from the voltage $U_C$ and the current I).

Furthermore, a redox potential measurement is preferably carried out based on a currentless measurement, wherein it is problematic that the supply line, as well as the measuring electrode 6 itself, tends to represent an antenna, which generates interfering signals and moreover enables interfering electrochemical current flows. So as to reduce such influence, the measuring electrode or the second electrode 6 can be shielded by a shield electrode, here in the form of the first electrode 5, which, for example, electrically tracks the measured potential of the second electrode 6.

Figure 5:
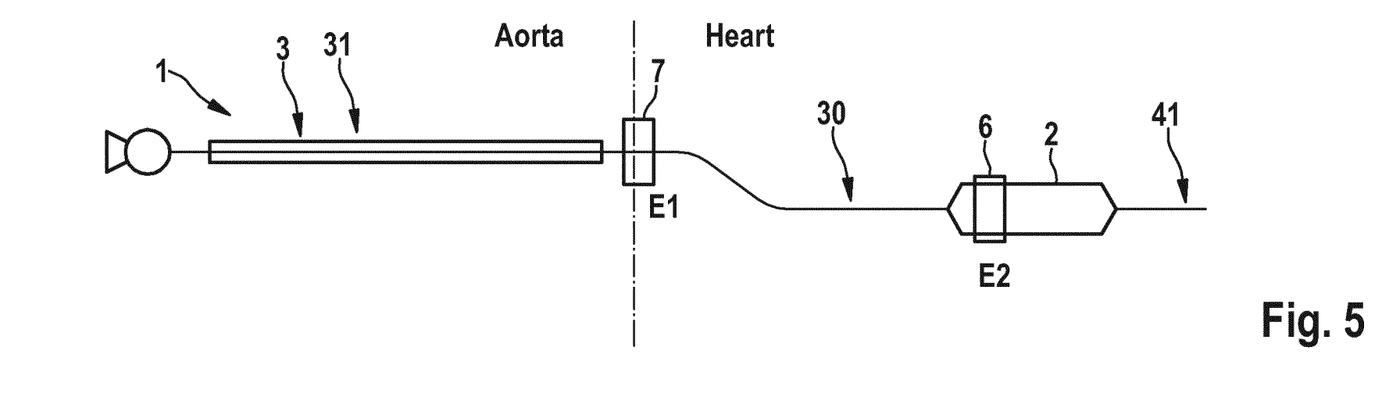
FIG. 5 shows a schematic representation of an embodiment of a balloon catheter system according to the invention, which is, in particular configured for redox potential measurement.
Figure 6:
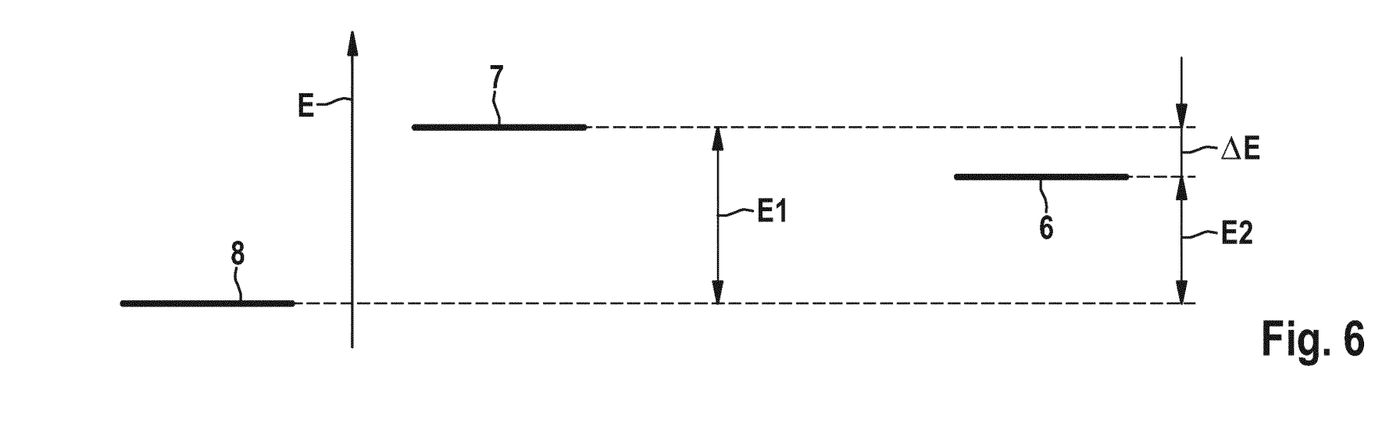
FIG. 6 shows a schematic representation of a measurement of a relative redox potential by a differential measurement or the measurement of a redox potential using a reference electrode (known reference potential).

FIGS. 5 and 6 show an arrangement for measuring a relative redox potential ΔE by a balloon catheter system 1 according to the invention, wherein for this purpose the system 1 includes a third electrode 7, which is preferably made of the same material as the second electrode 6 (FIG. 1) and, for example, is disposed at one end of the guide shaft 31 of the catheter 3, so that the third electrode 7, for example during implantation of the stent 9, becomes positioned, in particular, at the transition from the aorta to the heart of the patient. Since no significant exchange of blood is present here, the respiratory modulation can be measured based on a difference ΔE between the redox potential E1 measured by way of the third electrode 7, and the redox potential E2 measured by way of the second electrode 6 (see FIG. 6). Instead of the third electrode 7, it is also possible, of course, to use a known reference potential (such as calomel electrode) 8 so as to provide an absolute redox potential measurement.

The above-described measurements/evaluations can be carried out by a measuring device 70 of the balloon catheter system 1 (see FIG. 2), which is connected in the above-described manner to the two electrodes 5, 6 by way of the conductors L1, L2, L3, for example (see FIG. 1). The measuring device 70 is, in particular, designed to appropriately activate the is electrodes 5, 6 by way of the conductors L1, L2, L3 or contact regions A, B, C for carrying out the individual measurements. In the case of an arrangement in the manner of FIG. 5, the measuring device 70 can furthermore be suitably connected to the third electrode 7.

In summary, the electrode arrangement according to the invention advantageously provides three measuring techniques on the balloon surface, and more particularly radial strain measurement or strain measurement in the circumferential direction of the balloon (balloon diameter), bioimpedance measurement on the vessel wall (expanded) or on the balloon surface, and furthermore the implementation of a redox electrode.

This advantageously allows increased dimension monitoring and the implementation of a diameter behavior of the balloon that is not directly proportional to the pressure. Furthermore, it is possible to detect atherosclerotic changes in the contact tissue during the dilation of the balloon. Furthermore, the blood perfusion around the catheter during placement thereof can be detected. This allows, in particular, a shifting of the stent to be detected, or oxygen depletion or oxidative stress to be detected in the vascular tissue (under intensive contact) or in the surrounding blood flow.

The invention claimed is:

1. A balloon catheter system comprising:
   a balloon extending in an axial direction and surrounding a balloon interior, the balloon having an outer side facing away from the balloon interior;
   a catheter connected to the balloon and extending in the axial direction, the catheter having a lumen in fluid communication with the balloon interior; and
   first and a second annular electrodes disposed on the outer side, each extending in a circumferential direction of the balloon and being located opposite one another in the axial direction, wherein the first electrode has an open annular design and the second electrode has a closed annular design, wherein the first electrode comprises first end portions located opposite one another in an axial direction, wherein the first electrode comprises second end portions joined by a joining section that extends in the axial direction, wherein the first end portions are located opposite the joining section in the circumferential direction to define a gap, and wherein the second electrode comprises a protrusion that extends through the gap;
   the electrodes being configured to measure one of more of strain of the balloon in the circumferential direction, strain of the balloon in the radial direction, an impedance of tissue of a patient resting against the electrodes, and a redox potential of tissue of the patient contacting at least one of the electrodes.

2. The balloon catheter system according to claim 1, wherein the first electrode includes a first section and second section extending in the circumferential direction, wherein the second section runs along the first section and is located opposite the first section in the axial direction.

3. The balloon catheter system according to claim 1, wherein the second end portions and joining section form a first contact region, the protrusion forms a second contact region and one of the first end portions forms a third contact region.

4. The balloon catheter system according to claim 3, wherein the first, second and third contact regions are connected to first, second and third conductors.

5. A balloon catheter system comprising:
   a balloon extending in an axial direction and surrounding a balloon interior, the balloon having an outer side facing away from the balloon interior;
   a catheter connected to the balloon and extending in the axial direction, the catheter having a lumen in fluid communication with the balloon interior; and
   first and a second annular electrodes disposed on the outer side, each extending in a circumferential direction of the balloon and being located opposite one another in the axial direction;
   the electrodes being configured to measure one of more of strain of the balloon in the circumferential direction, strain of the balloon in the radial direction, an impedance of tissue of a patient resting against the electrodes, and a redox potential of tissue of the patient contacting at least one of the electrodes, wherein the first electrode includes a first section and second section extending in the circumferential direction, wherein the second section runs along the first section and is located opposite the first section in the axial direction, wherein the first section has a first end section and a second end section, and the second section has a first end section and a second end section, the first and second end sections of the first electrode being joined to one another by a joining section that extends in the axial direction.

6. The balloon catheter system according to claim 5, wherein the first section of the first electrode is covered by electrical insulation.

7. The balloon catheter system according to claim 6, wherein the first end section of the first section of the first electrode and the first end section of the second section of the first electrode are located opposite one another in the axial direction.

8. The balloon catheter system according to claim 7, wherein the first end section of the first section of the first electrode and the first end section of the second section of the first electrode are located opposite the joining section in the circumferential direction such that a gap is formed between the two first end sections and the joining section.

9. The balloon catheter system according to claim 8, wherein the second electrode includes a protrusion that projects from an annular region of the second electrode in the axial direction and extends in the axial direction into the gap, such that the protrusion is disposed in the circumferential direction between the joining section and the two first end sections of the first electrode.

10. A balloon catheter system according to claim 9, wherein the second end section of the first section of the first electrode forms a first contact region of the first electrode that is conductively connected to a first conductor.

11. A balloon catheter system according to claim 10, wherein the protrusion forms a contact region of the second electrode that is conductively connected to a second conductor.

12. A balloon catheter system according to claim 11, wherein the first end section of the first section of the first electrode forms a second contact region of the first electrode that is conductively connected to a third conductor.

13. The balloon catheter system according to claim 12, wherein the balloon catheter system is configured to measure the impedance through a voltage on the second contact region.

14. The balloon catheter system according to claim 13, wherein the balloon catheter system is configured to measure the redox potential through a voltage on the contact region of the second electrode.

15. A balloon catheter system according to claim 13, comprising a stent crimped onto the outer side of the balloon, the stent being expandable by expansion of the balloon.

16. The balloon catheter system according to claim 15, wherein the stent is spaced apart from the two electrodes in the axial direction.

17. A method using a balloon catheter system comprising a balloon catheter system comprising:
   a balloon extending in an axial direction and surrounding a balloon interior, the balloon having an outer side facing away from the balloon interior;
   a catheter connected to the balloon and extending in the axial direction, the catheter having a lumen in fluid communication with the balloon interior; and
   first and a second annular electrodes disposed on the outer side, each extending in a circumferential direction of the balloon and being located opposite one another in the axial direction;

the electrodes being configured to measure one of more of strain of the balloon in the circumferential direction, strain of the balloon in the radial direction, an impedance of tissue of a patient resting against the electrodes, and a redox potential of tissue of the patient contacting at least one of the electrodes wherein the method comprises measuring strain of the balloon in the circumferential direction of the balloon or in the radial direction of the balloon with the first electrode, measuring impedance with the first and second electrodes, and measuring redox potential with the second electrode.

* * * * *